(12) United States Patent
Bos et al.

(10) Patent No.: US 8,197,851 B2
(45) Date of Patent: Jun. 12, 2012

(54) CAROTENOID COMPOSITION AND METHOD FOR PREPARATION THEREOF

(76) Inventors: Michael Ary Bos, Pearcedale (AU); David Graham Ellis, Mount Waverley (AU)

( * ) Notice: Subject to any disclaimer, the term of this patent is extended or adjusted under 35 U.S.C. 154(b) by 274 days.

(21) Appl. No.: 11/576,276

(22) PCT Filed: Sep. 29, 2005

(86) PCT No.: PCT/AU2005/001515
§ 371 (c)(1),
(2), (4) Date: May 16, 2007

(87) PCT Pub. No.: WO2006/034556
PCT Pub. Date: Apr. 6, 2006

(65) Prior Publication Data
US 2007/0269526 A1    Nov. 22, 2007

(30) Foreign Application Priority Data

Sep. 29, 2004 (AU) ............... 2004905670

(51) Int. Cl.
*A61K 9/14* (2006.01)
(52) U.S. Cl. .................................................. 424/489
(58) Field of Classification Search ............. None
See application file for complete search history.

(56) References Cited

U.S. PATENT DOCUMENTS

| | | | |
|---|---|---|---|
| 5,827,539 A | 10/1998 | Gellenbeck | |
| 5,863,953 A * | 1/1999 | Luddecke et al. | 514/691 |
| 6,235,315 B1 | 5/2001 | Runge et al. | |
| 6,544,532 B1 * | 4/2003 | Jager-Lezer et al. | 424/401 |
| 6,936,279 B2 | 8/2005 | Guerra-Santos et al. | |
| 7,056,525 B2 * | 6/2006 | Runge et al. | 424/439 |
| 7,105,176 B2 * | 9/2006 | Auweter et al. | 424/439 |
| 7,879,360 B2 * | 2/2011 | Cunningham et al. | 424/489 |
| 2003/0050283 A1 * | 3/2003 | Richter et al. | 514/78 |
| 2004/0191365 A1 | 9/2004 | Leuenberger | |

FOREIGN PATENT DOCUMENTS

| | | |
|---|---|---|
| WO | 96/23420 A | 8/1996 |
| WO | 03/017785 A | 3/2003 |
| WO | 03/105807 A | 12/2003 |
| WO | WO 03/105807 * | 12/2003 |
| WO | WO 03105807 A1 * | 12/2003 |

OTHER PUBLICATIONS

Tapiero et al., The role of carotenoids in prevention of human pathologies. Biomedicine & Pharmacotherapy 58: 100-110 (2004).*
Kritchevsky, beta-Carotene, Carotenoids and the Prevention of Coronary Heart Disease, J Nutrition 129: 5-8 (1999).*
Schwartz et al., Prevention of experimental oral cancer by extracts of Spirulina-Dunaliella algae, Nutr Cancer 11: 127-34 (1988).*
Schwartz et al., Nutr. Cancer 11: 127 (1988).*

* cited by examiner

*Primary Examiner* — Johann Richter
*Assistant Examiner* — Thor Nielsen
(74) *Attorney, Agent, or Firm* — LeClairRyan, a Professional Corporation

(57) ABSTRACT

This invention relates to a carotenoid composition comprising the carotenoid as particles of size smaller than 100 nanometers in an oil medium, a method of preparing the composition by milling the carotenoid in an oil medium, and therapeutic compositions containing the carotenoid.

16 Claims, 2 Drawing Sheets

NUMBER – Weighted NICOMP DISTRIBUTION Analysis (Solid Particle)

NUMBER – Weighted NICOMP DISTRIBUTION Analysis (Solid Particle)

8,197,851 B2

CAROTENOID COMPOSITION AND METHOD FOR PREPARATION THEREOF

This application is a national stage application under 35 U.S.C. §371 from PCT Application No. PCT/AU2005/001515, filed Sep. 29, 2005, which claims priority from Australian Provisional Application No. 2004905670 filed on Sep. 29, 2004, the contents of which are to be taken as incorporated herein by this reference.

This invention relates to a carotenoid composition, to a method of preparation thereof and to use of the compositions in various applications.

BACKGROUND

Carotenoids can be divided into two classes: —carotenes (polyene hydrocarbons) such as beta-carotene and lycopene, and xanthophylls (oxygenated carotenoids) such as lutein and astaxanthin. These carotenoids are moderately soluble in oil and are insoluble in water, these polyethers are important pigments for food, feed and pharmaceutical industries.

As well as being used for pigments some carotenoids have nutritional value, e.g. beta carotene is a vitamin A precursor and astaxanthin has provitamin A activity in salmon.

Carotenoids are very susceptible to oxidation and heat and will react with oxygen in the air to render them inactive and colourless.

A number of workers have prepared formulations of carotenoids for therapeutic use including the work reported in the documents discussed below. However a reference herein to a patent document or other material which is mentioned as prior art is not to be taken as an admission that that document or material was published or known or that the information it contains was part of the common general knowledge as at the priority date of any of the claims.

U.S. Pat. No. 5,460,823 (Jansen et al) relates to a process of preparing microparticles of carotenoids in which solids are milled in an aqueous medium in the presence of a hydrocolloid. The mixture is spray dried to form microparticles of maximum particle size of about 10 microns.

U.S. Pat. No. 5,811,609 (Vilstrup et al) likewise prepares particles by milling carotenoids in aqueous medium to form a suspension in the presence of a hydrocolloid. The suspension is heated to cause melting of the carotenoid which is spray dried to form a powder.

U.S. Pat. No. 6,639,113 (Runge et al) describes the preparation of powdered oxygenated carotenoids such as astascanthin which are formed by dissolving the composition of the oxygenated carotenoid in a solvent at 50° C. to 240° C. which is mixed with a protecting colloid and set before conversion to a powder by spray drying or the like methods. Chimia 21,329 (1967), (see also DE Application No. 12 11 911 and DE Publication No. 25 34 091 disclose methods of dissolving the active compound in a chlorinated organic solvent, emulsifying the solution in a gelatine/sucrose solution and extracting the solvent from the emulsion causing the active compound to crystallize in microcrystalline form. A disadvantage of this method is that it is technically impossible to remove the organic solvent completely and the solvent is a potential hazard during the process and as residues in the final product.

U.S. Pat. No. 5,827,539 (Gellenback at al) prepares a dry carotenoid powder by grinding in an oil to provide particles of about 0.5 microns which are dispersed in an aqueous encapsulating media. Emulsification and drying need to be controlled to avoid the formation of sticky agglomerates of poor stability.

U.S. Pat. No. 6,132,790 (Schlipalius) describes a carotenoid in an oil solvent which is dispersed in an aqueous phase in the presence of an emulsifier to provide fine droplets of oil phase.

U.S. Pat. No. 5,773,026 (Schlipalius) describes use of a natural carotenoids oil composition in a non-toxic water dispersible therapeutic formulation suitable for injection or intravenous use by humans or animals.

U.S. Pat. No. 6,428,816 (Schlipalius et al) describes treatment of melanoma or melanomas by injection of a water insoluble carotenoid component and a mixture of a water dispersible component.

U.S. Pat. No. 5,780,056 (Akamatsu et al) describes natural carotenoid formulated as capsules having a multi core structure provided by heating the carotenoid to 120° C. in an oil and cooling to 70° C. before forming a water in oil emulsion and inverting the phases and encapsulating the resulting oil-in-water emulsion as microfine oil particles.

Naturally sourced oils containing carotenoids such as palm oil, carrot oil etc contain a mixture of carotenoids e.g. alpha carotene, beta-carotene, gamma carotene, lycopene in solubilised form and particulate form. When the oils are refined, these carotenoids are lost or degraded and therefore have a low level of bioavailability.

There is a need for a stable carotenoid composition of high biological activity.

SUMMARY

We have found that by intensive milling to reduce the particle size of carotenoids suspended in an oil medium to a size smaller than 100 nanometers, preferably 10 to 70 nanometers, more preferably to 20-50 nanometers we can increase the bioavailability of the carotenoid, whilst at the same time we can improve the long-term stability of the suspensions.

We have further found that we can add oil soluble antioxidants during the milling stage with enhanced protection for the suspended carotenoids.

We have also found that the milled product when used in creams for use on the skin allows absorption of the carotene, typically beta-carotene through the epidermis and is absorbed into the blood stream. This will give enhanced protection against melanomas on the skin and can be used in sunscreen, moisturizer and other skin care products where the reduction in free radicals improves skin protection. The composition may also be used as a dietary supplement in the form of tablets, syrups, powders and liquids and may be taken with food or beverages.

This milled product can also be used in sprays or drops in combating dryness in the eyes, mouth and nose particularly in elderly people.

Use of this milled product when used in animal feeds, such as feed for larval fish gives increased protection against liver rupture.

In accordance with a first aspect the invention provides a method for preparing a carotenoid composition comprising milling the carotenoids in an oil medium to provide carotenoid particles of size smaller than 100 nanometers (preferably from 1 to 70 nanometers and more preferably from 2 to 50 nanometers).

In accordance with a second aspect we provide a carotenoid composition comprising particles of one or more carotenoids of size smaller than 100 nanometers (preferably from 1 to 70 nanometers, more preferably 2 to 50 nanometers) formed by milling one or more carotenoids in an oil medium.

In a third aspect we provide the use of a composition for transdermal administration of one or more carotenoids comprising particles of said one or more carotenoids of size smaller than 100 nanometers (preferably from 1 to 70 nanometers and more preferably from 2 to 50 nanometers) dispersed in an oil medium by milling therein.

In a fourth aspect we provide the use of a composition for combating dryness of a part of the body such as the eyes, mouth or nose the use comprising applying a composition of at least one carotenoid comprising particles of said one or more carotenoid of size smaller than 100 nanometers (preferably from 1 to 70 nanometers and more preferably from 2 to 50 nanometers) dispersed in an oil medium by milling.

In a fifth aspect we provide the use of the above-described carotenoid composition as an antioxidant for a food. Examples of such food compositions include dairy foods, confectionery, wines, soft drinks, packaged foods and baking products.

DETAILED DESCRIPTION

The present invention relates to milling carotenoids dispersed in oils to a particle size below 100 nm. We have found that the resulting carotenoids typically provide enhanced stability and bioavailability. In many cases the antioxidant properties are enhanced.

Examples of suitable carotenoids for use in the invention include
- Beta-carotene which is widely used as a food colouring ingredient and which has special properties in biological products, by quenching oxygen and reducing free radicals
- Astaxanthin imparts its red colour to the flesh of salmonoids and shells of shrimps and crayfish.
- Lutein, like beta-carotene, is a carotenoid. Lutein is one of the most abundant carotenoids found in fruits and vegetables. Lutein is also an antioxidant found in the retina of healthy eyes.
- Zeaxanthine, like lutein and beta-carotene, is a carotenoid. Zeaxanthine is found naturally in fruits and vegetables. Zeaxanthine is also a biological antioxidant and is found for example in the retina of healthy eyes.

Beta-carotene is the preferred carotene for use in the invention but the optimum composition may depend on the use and delivery method. The carotenoid component will preferably comprise at least 20% by weight, more preferably at least 40% by weight and most preferably at least 50% by weight of beta-carotene.

Each carotenoid has its own special properties when used separately, but these properties are sometimes reduced when carotenoids are mixed together. Compositions may be formed for different application directly from the milled oil mixture by further formulation, for example by emulsification of oil mixture of the natural carotenoids with an aqueous phase.

In one embodiment the beta-carotene is a mixture of cis beta-carotene and all trans beta-carotene. Typically, the cis beta-carotene content of the beta-carotene is in the range of 50% and 90%, more preferably 70% and 85%. It may be preferred in some embodiments that the beta-carotene is predominantly 9 cis beta-carotene in a preferred range of 60% to 90%.

The composition may in another embodiment comprise a mixture of nanoparticulate carotenoids from natural sources. For example one particularly useful mixture comprises:
- about 60-70% all trans beta carotene
- about 30-40% cis beta carotene 9-cis, 13-cis, 15-cis, di-cis
- about 1 to 5% and preferably 3-5% α-carotene
- about 1 to 5% and preferably about 2% xanthophylls (lutein, zeoxanthin, crypotoxanthin)

the percentages being present by weight of components based on the total weight of carotenoid components.

The composition of the invention may comprise one or more additional active components selected, for example from one or more of vitamins, minerals and antioxidants.

Various terms are used in the specification and claims and except where the content calls for another meaning the terms have the meanings provided below.

Throughout the description and the claims of this specification the word "comprise" and variations of the word, such as "comprising" and "comprises" is not intended to exclude other additives, components, integers or steps.

The term "vitamin" as it is used herein, is intended to mean a micronutrient that acts generally in small amounts in the regulation of various metabolic processes but generally do not serve as an energy source or as a building unit. Vitamins are ordinarily ingested on a regular basis or stored in quantity in humans due to deficiencies in biosynthetic capacity. Specific examples of vitamin micronutrients include vitamins A, B, C, D and E.

The term "mineral" as it is used herein, is intended to mean a naturally occurring homogeneous or apparently homogeneous and generally solid crystalline chemical element or compound that results from inorganic processes of nature having a characteristic crystal structure and chemical composition. Specific examples of mineral and chemical element micronutrients include zinc, iron, iodine and boron.

The term "antioxidant" as it is used herein, is intended to mean a substance that opposes oxidation or inhibits reactions promoted by, for example, oxygen, peroxides or free radicals. Specific examples of antioxidant micronutrients include vitamin C, bioflavonoid complex, vitamin E and vitamin B6. Specific examples of cofactor micronutrients include vitamin B1, vitamin B2 and vitamin B6. Preferred antioxidants include tocopherol and esters of ascorbic acid e.g. ascorbic palmitate and stearate.

The term "milling" as used herein means mechanically reducing in size for example, by breaking, crushing or grinding in known mills such as autogenous mills involving tumbling or more preferably mills containing additional media such as steel balls or rods.

As used herein, the term "preservative" means a compound used to prevent the growth of microorganisms or prevent the degradation of one or more active ingredients. Such compounds include, by way of example and without limitation, benzalkonium chloride, benzethonium chloride, benzyl alcohol, cetylpyridinium chloride, chlorobutanol, phenol, phenylethyl alcohol, phenylmercuric nitrate and thimerosal and others known to those of ordinary skill in the art.

As used herein, the term "formulation antioxidant" means an agent which inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate and sodium metabisulfite and others known to those of ordinary skill in the art.

As used herein, the term "buffering agent" means a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and others known to those of ordinary skill in the art.

As used herein, the term "colorant" means a compound used to impart color to solid (e.g., tablets and capsules) pharmaceutical preparations. Such compounds include, by way of example and without limitation, FD&C Red No. 3, FD&C Red No. 20, FD&C Yellow No. 6, FD&C Blue No. 2, D&C Green No. 5, FD&C Orange No. 5, D&C Red No. 8, caramel, and ferric oxide, red and others known to those of ordinary skill in the art. Coloring agents can also include pigments, dyes, tints, titanium dioxide, natural coloring agents such as grape skin extract, beet red powder, beta carotene, annato, carmine, turmeric, paprika, CHROMAKOTE™ and others known to those of ordinary skill in the art.

As used herein, the term "flavorant" means a natural or artificial compound, or some combination of these, used to impart a pleasant flavor and often odor to a pharmaceutical preparation. Flavors incorporated in the composition may be chosen from natural and synthetic flavor oils and flavoring aromatics and/or natural oils, extracts from plants, leaves, flowers, fruits, and combinations thereof. Such compounds include, by way of example and without limitation, anise oil, cinnamon oil, vanilla, vanillin, cocoa, chocolate, menthol, grape, peppermint oil, oil of wintergreen, clove oil, bay oil, anise oil, eucalyptus, thyme oil, cedar leave oil, oil of nutmeg, oil of sage, oil of bitter almonds, cassia oil; citrus oils such as lemon, orange, lime and grapefruit oils; and fruit essences, including berry, apple, pear, peach, date, blueberry, kiwi, strawberry, raspberry, wildberry, cherry, plum, pineapple, and apricot. All of these flavorants are commercially available. Preferred flavorants include vanillin and berry. The amount of flavoring may depend on a number of factors, including the organoleptic effect desired.

As used herein, the term "sweetening agent" means a compound used to impart sweetness to a preparation. Such compounds include, by way of example and without limitation, aspartame, dextrose, glycerin, mannitol, saccharin sodium, sorbitol, sucrose high fructose corn syrup, fructose oligosaccharides, and others known to those of ordinary skill in the art.

As used herein, the term "tablet anti-adherents" means agents which prevent the sticking of iron supplement ingredients to punches and dies in a tabletting machine during production. Such compounds include, by way of example and without limitation, magnesium stearate, corn starch, silicone dioxide, talc and others known to those of ordinary skill in the art.

As used herein, the term "tablet binders" means substances used to cause adhesion of powder particles in tablet granulations. Such compounds include, by way of example and without limitation, acacia, alginic acid, carboxymethylcellulose sodium, compressible sugar (e.g., NUTAB™), ethylcellulose, gelatin, liquid glucose, methylcellulose, povidone, pregelatinized starch, those described above and others known to those of ordinary skill in the art.

As used herein, the term "tablet and capsule diluent" means inert substances used as fillers to create the desired bulk, flow properties, and compression characteristics in the preparation of tablets and capsules. Such compounds include, by way of example and without limitation, dibasic calcium phosphate, kaolin clay, fructose, sucrose, dextrose, lactose, mannitol, microcrystalline cellulose, powdered cellulose, precipitated calcium carbonate, sorbitol, calcium sulfate, starch and others known to those of ordinary skill in the art.

As used herein, the term "coating agent" means a compound used to coat a formed iron supplement for the purpose of protecting against active ingredient decomposition by atmospheric oxygen or humidity, to provide a desired release pattern for the active ingredient after administration, to mask the taste or odor of the active ingredient substance, or for aesthetic purposes. The coating may be of various types, including sugar coating, film coating, or enteric coating. Sugar coating is water-based and results in a thickened covering around a formed tablet. Sugar-coated tablets generally dissolve at the higher pH values of the intestines. A film coat is a thin cover around a formed tablet or bead. Unless it is an enteric coat, the film coat will dissolve in the stomach. An enteric coated tablet or bead will pass through the stomach and break up in the intestines. Film coatings such as those described above are included within this definition.

As used herein, the term "direct compression excipient" means a compound used in direct compression tablet formulations. Such compounds include, by way of example and without limitation, dibasic calcium phosphate (e.g., DITAB™), spray dried, or anhydrous lactose, microcrystalline cellulose, (AVICEL™), dextran (EMDEX™), sucrose (NUTAB™) and others known to those of ordinary skill in the art.

As used herein, the term "glidant" means agents used in tablet and capsule formulations to reduce friction during tablet compression. Such compounds include, by way of example and without limitation, colloidal or fumed silica, magnesium stearate, cornstarch, and talc and others known to those of ordinary skill in the art.

As used herein, the term "lubricant" means substances used in tablet formulations to reduce friction during tablet compression. Such compounds include, by way of example and without limitation, calcium stearate, magnesium stearate, mineral oil, stearic acid, hydrogenated vegetable oil, benzoic acid, poly(ethylene glycol), NaCl, PRUV™, zinc stearate and others known to those of ordinary skill in the art.

As used herein, the term "tablet/capsule opaquant" means a compound used to render a capsule or a tablet coating opaque. Opaquants can be used alone or in combination with a colorant. Such compounds include, by way of example and without limitation, titanium dioxide and others known to those of ordinary skill in the art.

As used herein, the term "polishing agent" means a compound used to impart an attractive sheen to coated tablets. Such compounds include, by way of example and without limitation, carnauba wax, and white wax and others known to those of ordinary skill in the art.

Functional food can be defined as any food that provides a health benefit beyond the traditional nutrients it contains. Such foods maintain and improve the state of health or well being of individuals, and or reduce the risk of diseases. Certain population groups need specific diet regimes such as infant food, sport nutrition or even medical nutrition.

The composition of the invention generally comprises an oil. Further the nanoparticulate carotene composition is preferable formed by milling in an oil. Suitable oils are generally fatty acid esters formed from $C_6$ to $C_{22}$ fatty acids. The alcohol component of the acid may be a $C_1$ to $C_{22}$ alcohol or polyol and mono-, di- and tri-glycerides and their mixtures are particularly preferred.

Examples of $C_6$-$C_{22}$ fatty acid esters with $C_6$-$C_{22}$-Fattyalcohols include Myristylmyristate, Myristylpalmitate, Myristylstearate, Myristylisostearate, Myristyloleate, Myristylbehenate, Myristylerucate, Cetylmyristate, Cetylpalmitate, Cetylstearate, Cetylisostearate, Cetyloleate, Cetylbehenate, Cetylerucate, Stearylmyristate, Stearylpalmitate, Stearylstearate, Stearylisostearate, Stearyloleate, Stearylbehenate, Stearylerucate, Isostearylmyristate, Isostearylpalmitate, Isostearylstearate, Isostearylisostearate, Isostearyloleate, Isostearylbehenate, Isostearyloleate, Oleylmyristate, Oleylpahnitate, Oleylstearate, Oleylisostearate, Oleyloleate, Oleylbehenate, Oleylerucate, Behenylmyristate, Behenylpalmitate, Behenylstearate, Behenylisostearate, Suitable esters of linear $C_6$-$C_{22}$ fatty acid esters with branched alcohols, in particular 2-Ethylhexanol. Oils include esters of hydroxy acids with linear or en branched $C_6$-$C_{22}$ fatty alcohols, in particular Dioctyl Malate. Suitable oils also include esters of linear and/or branched fatty acids with polyhydric alcohols (e.g. Propylenglycol, Dimerdiol or Trimertriol). Particularly preferred oils are the $C_6$ to $C_{22}$ fatty acid ester mono-, di-, tri-glycerides and mixtures thereof.

The oil used in the process of the invention is preferably an edible oil such as a refined plant oil, synthetic oils and phospholipids. Examples of plant oils include: canola, sunflower, peanut, soybean and corn oil. Examples of suitable synthetic oil include medium chain triglycerides, e.g. capric caprylic triglyceride produced from vegetable sources such as palm oil.

Phospholopids include lecithins.

The process of the invention involves milling a carotenoid component in the presence of an oil. Preferably the oil in which milling takes place is substantially free of water. More preferably the oil is free of water.

Milling may be achieved by any suitable method but will typically use intensive milling methods to economically provide the desired particle size within a reasonable time. Milling may be carried out using a ball mill, or other intensive mill such as a bead mill, attritor mill or sigma mixer.

Preferably the process of the invention is carried out by adding the carotenoid in a particulate form to the liquid whilst milling occurs although the carotenoid may be combined with the liquid and the mixture milled. The initial particle size of the carotenoid may be in the range of from 0.1 to 100 microns depending on the equipment used.

Preferably milling occurs at a temperature of less than 50° C. and preferably less than 35° C. to minimise the degradation of carotenoids. This is desirable to maintain optimum stability of the carotenoids. The carotenoids may present in an amount in the range of from about 0.1 to 95% of the liquid oil dispersion of the carotenoid. t is preferred to carry out milling under an inert atmosphere such as nitrogen or other inert gas.

In a further aspect, the present invention provides a liquid dispersion of a carotenoid in particulate form, wherein the carotenoid has a particle size in the range of about 1 to 70 nanometres and wherein the liquid is constituted by or includes a component which is a fatty acid ester, fatty alcohol, amide or mixture.

The carotenoid is preferably milled in the presence of an antioxidant which is preferably oil soluble. Examples of antioxidants include those referred to in the above definition. Vitamin E and its provitamins and derivatives are particularly preferred. The antioxidant is preferably present during the intensive milling in a weight ratio of antioxidant to carotenoid in the range of from 5:95 to 95:5 and more preferably from 5 to 150% and preferably 10 to 100% of the weight of the caratenoid. In many cases, such as for tocopherols we have found a weight ratio of 1 part antioxidant to 2 parts carotenoid to be particularly useful.

The carotenoid is preferably formed as a concentrate in the oil which may be used in preparing compositions of the invention for specific end uses which generally comprise a less concentrated carotenoid component than the milled concentrate.

Preferably the carotenoid is present in the concentrate dispersion in an amount of about 5% to 95% by weight. The carotenoid composition of the invention will typically comprise in the range of from 1 to 80% more preferably from 5 to 60% by weight of carotenoid based on the total weight of the oil milling medium and carotenoid. Preferably the carotenoid is present in an amount of at least about 10% by weight, more preferably greater than about 20% by weight of the dispersion. The surface area of the particulate carotenoid in the dispersion may be about 6 $m^2$ per gram of oxide to about 50 $m^2/g$, more preferably about 20 to about 30 $m^2/g$.

Preferably the liquid component of the dispersion is selected from an alcohol, ester, hydrogenated ester or a polymer containing available hydrogen ion, for example, hydroxyl groups or hydrogen groups or mixtures of one or more thereof.

The process of the invention provides a composition comprising carotenoid particles of size smaller than 100 nanometers. Preferably at least 80%, more preferably at least 90% and most preferably at least 95% of the carotenoid particles have a size smaller than 100 nanometers (preferably 1 to 70 nanometers, more preferably 2-50 nanometers.

Milled carotenoid oil concentrate is typically used in diluted compositions for the end use application at the levels of 0.00001 to 80%, more preferably from 0.0001 to 5% based on the carotenoid component of the concentrate composition.

Consumers are becoming increasingly critical regarding the efficacy of cosmetic and pharmaceutical products, additionally consumer buying indicates a preference for natural and nature-identical products. Cosmetic chemists are well aware of this back-to-nature preference, and now are more than ever seeking substances showing demonstrable beneficial effects.

First of all vitamins are known to be vital for the development and maintenance of the body, including the skin and hair.

Vitamins, such as vitamin E, and vitamin C are needed for the growth of new cells and healthy tissue.

In addition to their biological function, vitamins also possess physical and chemical properties which justify their use in topical preparations. For example, Vitamin E may be used as a powerful moisturizer, Tocopherol, the alcohol form of Vitamin E, and L-ascorbic acid may be incorporated to protect the preparations from oxidative damage.

Beta-carotene is involved in the maintenance of the structure and function of the epithelial and other tissues. Dermal symptoms of beta-carotene deficiency are defects in keratinization resulting in skin lesions and an abnormally dry and scaly skin.

Many people develop dry skin without any apparent deficiency in beta-carotene. This condition can be corrected by topical applications of nanoparticulate carotenoids.

An increase of epidermal cells through application of creams containing nanoparticulate carotenoids has a stimulating effect on the mitotic process in the skin. This is of special interest for aging skin since as a consequence of decreasing mitotic activity a thinning of the epidermis takes place in the elderly.

Peroxidation of lipids is one of the most damaging reactions for membranes and cellular constituents, such as proteins and DNA. Destruction of membrane lipids is a fundamental part of the aging process.

Degradation products of lipid peroxidation not only impair the function of the membranes but also damage other cell components. Breakdown products accumulate in lysosomes as lipofuscin, also called age pigment.

Initiation of lipid peroxidation is due to an attack by free radicals. Free radicals are highly reactive molecules that are produced in the human body in the course of normal biological reactions, and also by external factors such as radiation and pollutants. Peroxidation damage of cells may be controlled by antioxidants. In membranes lipid soluble Vitamin E and nanoparticulate carotenoids may be used to protect against peroxidation of polyunsaturated fatty acids by acting as a free radical chain breaker.

Pugliese treated hairless mice with emulsions of Vitamin E, and a mix of Vitamin E and beta-carotene respectively, exposed the animals to UV irradiation and compared the malonaldehyde produced in the skin with that of untreated control animals. Topical application of an emulsion containing 5% Vitamin E reduced the MDA content by 54%. Emulsions containing 0.05% beta carotene and 1% Vitamin E and 0.01% beta carotene and 2% Vitamin E decreases of 38% and 35% respectively, were observed.

These data indicate that Vitamin E and nanoparticulate carotenoids may play a role in attenuating the aging process of the skin.

Tocopherol sorbate is the tocopherol, more commonly known as Vitamin E, ester of sorbic acid. Alpha tocopherol (5,7,8-trimethyl tocol), beta tocopherol (5,8-dimethyl tocol), gamma tocopherol (7,8-dimethyl tocol), delta tocopherol (8-methyl tocol), epsilon tocopherol (5-methyl tocol), zeta tocopherol (5,7-dimethyl tocol), and eta tocopherol (7-methyl tocol) may be used to make tocopherol esters such as sorbate. Some of these isomers may be more efficacious for photoprotection than others. The beta, gamma and delta tocopherols exhibit particularly strong anti-oxidant properties and thus may be preferred for making the compositions of the present invention. Mixtures of these isomers may also be used.

The composition may, for example be in the form of a cream, gel, spray, ointment, lotion, balm, patch, or other suitable form.

More specific examples of the forms that the composition of the invention may take include hand and/or nail formulae, protein gel masque, sunburn lotion (i.e. after sun lotion) sunscreen lotion, body lotion, ointments, aerosols, sun gels, reparative creams and skin patches. The composition may be formulated according to techniques known in the art for use in specific skin areas such as the face, around the eyes, hands, feet etc.

Carotenoids are light absorbers making them suitable for use in sunscreen applications. Carotenoids are particularly suited to use in absorbing light in the visible region of the spectrum. The invention thus provides compositions of the invention in the form of sunscreens. The sunscreens may be oils, lotions, milks, creams or ointments. They may be in the form of an oil in water composition. These forms may be prepared from or include the oil composition used in preparing the nanoparticulate carotenoids. For example the milled composition may form at least a part of the oil carrier in a lotion or oil or it may provide all or part of a discontinuous oil phase of an oil in water emulsion.

The sunscreen comprising the carotenoids composition of the invention may and typically will include additional active sunscreens to provide complementary protection in other parts of the spectra and/or to enhance protection provided by the carotenoid component.

In this way the composition may provide reduce radiation by screening and also ameliorate the oxidative and damaging effects of radiation by virtue of the presence of carotenoids and optionally other components. Specific suitable additional sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipropyleneglycol esters); cinnamic acid derivatives (methyl and benzyl esters, alpha-phenyl cinnamonitrile; butyl cinnamoyl pyruvate); dihydroxycinnamic acid derivatives (umbelliferone, methylumbelliferone, methylaceton-umbilliferone); trihydroxycinnamic acid derivatives (esculetin, methylesculetin, daphnetin, and the glucosides, esculin and daphnin); hydrocarbons (diphenylbutadiene, stilbene); dibenzalacetone and benzlacetophenone; naphtholsulfonates (sodium salts of 2-naphthol-3,6-disulfonic and of 2-naphthol-6,8-disulfonic acids); dihydroxy-naphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (hydroxyquinoline salts, 2-phenylquinoline); hydroxy- or methoxy-substituted benzophenone; uric and vilouric acids; tannic acid and its derivatives (e.g. hexaethylether); (butyl carbotol) (6-propyl piperonyl)ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; 4-isopropyl-di-benzoylmethane, particulate titanium dioxide and particulate zinc oxide and other oxides.

The composition of the invention may comprise a nanoparticulate zinc oxide, titanium dioxide or iron oxide as described in our prior U.S. Pat. No. 6,083,490. A nanoparticulate metal oxide may be prepared by co-milling with the carotenoid if desired.

Compositions of the invention may comprise emollients to provide a carrier system suitable for use on skin. Typically the oil used in preparing the nanoparticulate carotenoid will provide part of the emollient component.

Examples of emollients include:
(i) Hydrocarbon oils and waxes. Examples include mineral oil, petrolatum, paraffin, ceresin, ozokerite, microcrystalline wax, polyethylene, and perhydrosqualene.
(ii) Silicone oils, such as dimethyl polysiloxanes, methylphenyl, polysiloxanes, water-soluble and alcohol-soluble silicone glycol copolymers.
(iii) Triglyceride esters, for example vegetable and animal fats and oils. Examples include castor oil, safflower oil, cottonseed oil, corn oil, olive oil, cod liver oil, almond oil, avocado oil, palm oil, sesame oil, and soybean oil.
(iv) Acetoglyceride esters, such as acetylated monoglycerides.
(v) Ethoxylated glycerides, such as ethoxylated glyceryl monostearate.
(vi) Alkyl esters of fatty acids having 10 to 20 carbon atoms. Methyl, isopropyl, and butyl esters of fatty acids are particularly useful herein. Examples of other useful alkyl esters include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.
(vii) Alkenyl esters of fatty acids having 10 to 20 carbon atoms. Examples include oleyl myristate, oleyl stearate, and oleyl oleate.
(viii) Fatty acids having 10 to 20 carbon atoms. Suitable examples include pelargonic, lauric, myristic, palmitic, stearic, isostearic, hydroxystearic, oleic, linoleic, ricinoleic, arachidic, behenic, and erucic acids.
(ix) Fatty alcohols having 10 to 20 carbon atoms. Lauryl, myristyl, cetyl, hexadecyl, stearyl, isostearyl, hydroxystearyl, oleyl, ricinoleyl, behenyl, and erucyl alcohols, as well as 2-octyl dodecanol, are examples of satisfactory fatty alcohols.

(x) Fatty alcohol ethers. Ethoxylated fatty alcohols of 10 to 20 carbon atoms include the lauryl, cetyl, stearyl, isostearyl, oeyl, and cholesterol alcohols having attached thereto from 1 to 50 ethylene oxide groups or 1 to 50 propylene oxide groups.

(xi) Ether-esters such as fatty acid esters of ethoxylated fatty alcohols.

(xii) Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

(xiii) Polyhydric alcohols and polyether derivatives. Propylene glycol, dipropylene glycol, polypropylene glycols 2000 and 4000, polyoxyethylene polyoxypropylene glycols, polyoxypropylene polyoxyethylene glycols, glycerol, sorbitol, ethoxylated sorbitol, hydroxypropyl sorbitol, polyethylene glycols 200-6000, methoxy polyethylene glycols 350, 550, 750, 2000 and 5000, polyethylene oxide homopolymers (100,000-5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), $C_{15}$-$C_{18}$ vicinal glycol, and polyoxypropylene derivatives of trimethylolpropane are examples of this class of materials.

(xiv) Polyhydric alcohol esters. Ethylene glycol mono- and di-fatty acid esters, diethylene glycol mono- and di-fatty acid esters, polyethylene glycol (200-6000) mono- and di-fatty acid esters, propylene glycol mono- and all-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters for use herein.

(xv) Wax esters such as beeswax, spermaceti, myristyl myristate, stearyl stearate and plant sources waxes such as macadamia oil wax and olive oil wax.

(xvi) Beeswax derivatives, e.g. polyoxyethylene sorbitol beeswax. These are reaction products of beeswax with ethoxylated sorbitol of varying ethylene oxide content, forming a mixture of ether-esters.

(xvii) Vegetable waxes including carnauba and candelilla waxes.

(xviii) Phospholipids, such as lecithin and derivatives.

(xix) Sterols. Cholesterol and cholesterol fatty acid esters are examples thereof.

(xx) Amides such as fatty acid amides, ethoxylated fatty acid amides, solid fatty acid alkanolamides.

The emollient may be derived at least in part from the oil in which the carotenoid component is milled.

A cream of the present invention would preferably comprise from about 0.1% to about 20%, more preferably from about 2% to about 5%, of the active compounds; from about 5% to about 50%, preferably from about 10% to about 20%, of an emollient, and from about 45% to about 85%, preferably from about 50% to about 75%, water.

A lotion can be made from a solution carrier system. Lotions preferably comprise from about 0.1% to about 20%, more preferably from about 2% to about 5%, of the active compounds; from about 1% to about 20%, preferably from about 5% to about 10%, of an emollient; and from about 50% to about 90%, preferably from about 60% to about 80%, water.

An ointment may also comprise from about 2% to about 10% of an emollient plus from about 0.1% to about 2% of a thickening agent. A more complete disclosure of thickening agents useful herein can be found in Segarin, Cosmetics, Science and Technology, 2nd Edition, Vol. 1, pp. 72-73 (1972).

The carotenoid composition of the invention may comprise an emulsion where the carotenoid is present as a dispersion of nanoparticles in the oil phase.

The oil phase may be the continuous phase of a water-in-oil emulsion or the discontinuous phase of an oil-in-water emulsion. Oil-in-water emulsions are generally preferred. The oil phase may be derived wholly or in part from the oil used in milling of the carotenoid.

If the carrier is formulated as an emulsion, from about 0.5% to about 10%, preferably from about 1% to about 5%, of the carrier system typically comprises an emulsifier. Emulsifiers may be nonionic, anionic or cationic. Suitable emulsifiers are described in McCutcheon's Detergents and Emulsifiers, (international Edition 1992) and Surfactants in Cosmetics 2nd edition, 1997, Marcel Decker Inc (pp 1 to 28) the disclosures of which are incorporated herein by reference. Preferred emulsifiers are anionic or nonionic, although the other types may also be used. Examples of useful nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene glycol wherein the fatty acid moiety contains from 10 to 20 carbon atoms, fatty acid monoglycerides wherein the fatty acid moiety contains from 10 to 20 carbon atoms, diethylene glycol, polyethylene glycols of molecular weight 200 to 6000, propylene glycol of molecular weight 200 to 3000, sorbitol, sorbitan, polyoxyethylene sorbitol, polyoxyethylene sorbitan and hydrophilic wax esters. Examples of such emulsifiers include polyoxyethylene (8) stearate, myristyl ethoxy (3) myristate, polyoxyethylene (100) monostearate, lauric diethanolamide, stearic monoethanolamide, hydrogenated vegetable glycerides, sodium stearoyl-2-lactylate and calcium stearoyl-2-lactylate. Suitable anionic emulsifiers include the fatty acid soaps, e.g., sodium, potassium, and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units.

Single emulsion skin care preparations, such as lotions and creams, of the oil-in-water type and water-in-oil type are well-known in the cosmetic art and are useful in the present invention. Multiphase emulsion compositions, such as the water-in-oil-in-water type, as disclosed in U.S. Pat. No. 4,254,105, Fakuda et al., issued Mar. 3, 1981, incorporated herein by reference, are also useful in the present invention. In general, such single or multiphase emulsions contain water, emollients and emulsifiers.

Another emulsion carrier system useful in the topical compositions of the present invention is a microemulsion carrier system. Such a system comprises from about 9% to about 15% squalane; from about 25% to about 40% silicone oil; from about 8% to about 20% of a fatty alcohol; from about 15% to about 30% of polyoxyethylene sorbitan monofatty acid (commercially available under the trade name Tweens) or other nonionics; and from about 7% to about 20% water. This carrier system is preferably combined with from about 2% to about 5% of the active compound.

Where they are to be used for transdermal administration compositions of the present invention may also include a safe and effective amount of a penetration-enhancing agent. A preferred amount of penetration enhancing agent is from about 1% to about 5% of the composition. Examples of useful penetration enhancers, among others, include $C_8$-$C_{36}$ fatty acids such as isostearic acid, octanoic acid, and oleic acid; $C_8$-$C_{36}$ fatty alcohols such as oleyl alcohol and lauryl alcohol; lower alkyl esters of $C_8$-$C_{36}$ fatty acids such as ethyl oleate, isopropyl myristate, butyl stearate, and methyl laurate; di(lower) alkyl esters of $C_6$-$C_8$ diacids such as diisopropyl adipate; monoglycerides of $C_8$-$C_{36}$ fatty acids such as glyceryl monolaurate; tetraglycol (tetrahydrofurfuryl alcohol polyethylene glycol ether); tetraethylene glycol (ethanol,2,2'-(oxybis(ethylenoxy))diglycol); $C_6$-$C_{36}$ alkyl pyrrolidone carboxylates; polyethylene glycol; propylene glycol; 2-(2-ethoxyethoxy)ethanol; diethylene glycol monomethyl ether; N,N-dimethyldodecylamine-N-oxide and combinations of the foregoing. Alkylaryl ethers of polyethylene oxide, polyethylene oxide monomethyl ethers, and polyethylene oxide dimethyl ethers are also suitable, as are solubilizers such as glycerol and N-methylpyrrolidone. The terpenes are another useful class of additives, including pinene, d-limonene, carene, terpineol, terpinen-4-ol, carveol, carvone, pulegone, piperitone, menthone, menthol, neomenthol, thymol, camphor, borneol, citral, ionone, and cineole, alone or in any combination. Of the terpenes, terpineol, particularly α-terpineol, is preferred.

The composition of the invention may be in the form of a spray. The spray may be delivered from a pump actuated spray device or from a pressurized aerosol container with a suitable propellant such as a hydrocarbon, chlorofluorocarbon, hydrochlorofluorocarbon or hydrofluorocarbon. HFCs such as R134a are particularly suitable. The carrier for a spray may contain a suitable solvent in addition to the propellant.

Human epidermis contains endogenous retinoids (retinol and retinyl esters) and carotenoids (mostly beta-carotene). Studies have shown that the enzymes involved in retinoid metabolism are present in human epidermis, however, there is still controversy about the presence in the skin of the enzymes able to convert beta-carotene into retinol. Antille C A et al, demonstrated that topical beta carotene penetrated well into well into human epidermis (ex vivo) and mouse epidermis (in vivo) and induced a 10-fold (human) and 3-fold (mouse) increase of epidermal retinyl esters, which demonstrates that topical beta carotene is converted into retinyl esters by human and mouse epidermis, and therefore appears to be a precursor of epidermal Vitamin A.

Beta-carotene works as an agonist of Vitamin A by reversibly sticking the chemical mechanism of melanogenesis by saturating the nuclear receptors of melanocytes and/or binding protein. Kar H K, used a beta-carotene lotion topically on melasma on 31 adults. This study concluded that topical applications of beta-carotene lotion was an effective and safe treatment for melasma, with longer durations of applications associated with better results.

Data reviewed from clinical studies and clinical trials indicate that most of these studies were conducted using either synthetic or standard commercially available carotenoids, having a particle size significantly greater than 100 (preferable 70) micron.

The compositions of the present invention provide a significant improvement in bioavailability of carotenoids improving the effectiveness when applied topically or orally to skin or mucous membranes or when administered by oral ingestion. Previous studies of the bioavailability generally use higher dose levels (30 mg to 90 mg) to improve the performance of the carotenoids. These dose levels are restrictive due to:

1. Adverse reactions, e.g. smokers would be restricted using carotenoids; and
2. Colour change in the dermis and epidermis, an undesirable side effect.

High doses may be also more invasive when taken for extended periods. On the other hand, nanoparticulate carotenoids with their improved bioactivity would be more effective resulting in lower dose levels such as 5 mg to 20 mg. We now have improved bioactivity increasing the potential for use in a wide range of oral and topical and other dose forms, offering improved economical system.

Medium Chain Triglycerides (MCT) act as a stable carrier for a wide range of actives such as Vitamins A, E C and B and carotenoids. MCT have a number of advantages including providing a first energy source, improving digestion, providing high levels of lipids and providing phytoesterols for nutrition and topical application. They are particularly useful as carriers in compositions of the invention containing nanoparticulate carotenoids and optionally further containing one or more of at least one supplement selected from vitamins and minerals.

MCT are not only a good carrier, but it also stabilizes and improves bio effectiveness of the above actives. The flexibility of MCT can be further enhanced and increased when combined with emulsifiers to act as a carrier system to enhance functional foods.

The functional food market is a growth area due to factors such as;
Economist predictions of increasing health care costs
Demographics indicating an aging population
Encouragement by governments for healthier lifestyles, with new legislations enabling food companies to increase the level of actives in foods
Emerging science, showing increasing evidence of the health benefits of certain ingredients.

Today's lifestyle and the increasing consumption of fast foods, combined with the reduction in consumption of fresh fruit and vegetables containing carotenoids is now creating a wide range of health problems that will place a greater economic loading on our health care system.

Nanoparticulate carotenoids improve bio-effective pro-vitamin A properties over other forms of carotenoids and so provides a significantly improved dietary supplement.

By milling carotenoids in capric caprylic triglyceride, or other food suitable oils, the carrier system also provides an energy source, improves digestion, provides high levels of lipids and may include phytosterols for digestion.

Nanoparticulate carotenoids can be safely and effectively used as a pro-vitamin A source in functional foods and medical nutrition. Typically it is used in amounts of from 0.001 to 2%. In specific applications the following are preferred.

| Application | % |
|---|---|
| Clinical nutrition | 0.001-0.1 |
| Dietetic food | 0.001-0.1 |
| Sports nutrition | 0.01-0.1 |
| Wellness drinks | 0.001-0.01 |
| Pharmaceutical | 0.001-0.8 |

The crystal size in such applications is preferably from 1-70 nm.

Nanoparticulate carotenoids can be readily added to a wide range of foods as a supplement that may bridge the dietary gap between what people should be eating and what people are actually eating. Nanoparticulate carotenoids supplements provide a convenient and relatively inexpensive means of fortifying the diet with a known dose of carotenoids in a high bio-available form, crystal size from 1-70 nm. Dose rate will vary depending on the specific application in food supplementation.

The nanocarotenoid composition of the invention may be in the form of dietary supplement for oral administration and may take the form of, for example, a capsule, lozenge tablet, chewable tablet, syrup, granule, water dispersible particles or drink. The composition may contain suitable carriers, excipients and fillers known in the art for formulating such compositions.

One example of a vitamin supplement includes the composition containing:
(a) about 100-6000 International Units (I.U.) of nanoparticulate beta-carotene (preferably about 1000-2200 I.U.); and one or more of
(b) about 1-100 milligrams of iron;
(c) about 0.1-2.0 milligrams of folic acid (preferably at least about 1-1.2 milligrams);
(d) about 0.2-8 milligrams of vitamin $B_1$ (preferably at least about 2-2.4 milligrams);
(e) about 0.5-10 milligrams of vitamin $B_2$ (preferably at least about 3-3.45 milligrams);
(f) about 2-50 milligrams of vitamin $B_6$ (preferably at least about 10-12 milligrams);
(g) about 2-20 micrograms of vitamin $B_{12}$ (preferably at least about 12-14.4 milligrams);
(h) about 20-200 milligrams of vitamin C (preferably at least about 120-132 milligrams);
(i) about 100-800 I.U. of vitamin $D^3$ (preferably at least about 400-440 I.U.);
(j) about 1-50 I.U. of vitamin E (preferably at least about 11-12 I.U.); and
(k) about 5-40 milligrams of one of niacin and niacinamide (preferably at least about 20-22 milligrams of niacinamide or an equivalent molar amount of niacin).

The composition may include one or more additives such as formulation antioxidants, preservatives, buffering agents, colourants, flavourants, sweetening agents, tablet anti-adherents, capsule and tablet diluents, coating agents, direct compression excepients, glidants, lubricants, tablet/capsule opaque and polishing agents.

The composition of the invention may be in the form of a particulate for mixing with food or drink. An example of such a composition may comprise a non-dairy creamer including an oil or low melting fat (less than 80° F.), for example in an amount of 10 to 50%; carbohydrate source in an amount for example of from 10 to 80%; sodium caseinate preferably in an amount of from 3 to 15 wt %; and a gum in an amount of for example 0 to 10%.

The low melting fat may comprise a partially hydrogenated vegetable oil such as coconut oil, cottonseed oil, palm kernel oil, soybean oil, canola oil, palm oil or mixtures thereof. The oil may comprise at least part of the oil component used to form the nanoparticulate carotenoid composition. Generally the oil/fat will include at least a portion having a melting point of at least 0° C.

The carbohydrate source may comprise maltose, dextrose, glucose, sucrose, corn syrup solids and mixtures thereof. Corn syrup solids are preferred. The carbohydrate component of the nutritional dry may comprise from about 40 to 60 wt % of the total weight of the dry mix.

If a gum is employed in the non-dairy creamer, acacia, agar, carrageenan, sodium alginate, xanthan gum or cellulosic gums such as methyl cellulose, hydroxy ethyl cellulose, hydroxypropyl cellulose, hydroxypropyl methylcellulose, and mixtures thereof. The gums also include carboxymethylcellulose which is the preferred gum.

The dry mix may also contain from 0.1 to 1 wt % of the gum, based on the total weight of the dry mix, as a stabilizer.

A comestible organic acid may be added in an amount of 1 to 3 wt %, based on the weight of the dry mix to provide a pH of about 3.3-4.0 in the product produced when the dry mix is added to water or a juice. The organic acids include malic acid, tartaric acid, fumaric acid, citric acid and mixtures thereof. The acid is added to improve the taste of the nutritional beverage and to mask the taste of the vitamins which are added to the drink mix.

Fiber such as soluble fiber derived from gum acacia pine fiber, oat fiber and the like in an amount of 2 to 10 wt % based on the total weight of the drink mix. Certified color may be added to obtained the desired color in the final product.

The dispersant may be any food grade acceptable dispersant such as soya lecithin, polysorbate 20, polysorbate 40, polysorbate 60, polysorbate 80 and the like. It may be used in an amount of 0.1 to 1 wt % based on the weight of the dry mix.

In another example the composition of the invention is in the form of a flavoured drink powder such as a powder for making a chocolate drink. A specific example of such a composition may, in accordance with the disclosure of U.S. Pat. No. 5,002,779 (Mehansho) comprise:
(a) from 0% to about 25% milk solids, preferably nonfat milk solids;
(b) from about 0.05% to about 20% flavor, preferably, cocoa;
(c) from 0.001 to 5% nanoparticulate carotenoid supplement; and
(d) from about 0.5% to about 85% sweetener.

A stable dry mixes may include in addition to the nanoparticulate carotenoid component other vitamins and minerals such as vitamin C to enhance the body's uptake of nutritionally supplemental amounts of iron compounds in humans and lower animals. These dry beverage mixes can be supplemented with vitamin A, vitamin E, vitamin D and the B vitamins, e.g., riboflavin, niacin, pantothenic acid, folic acid and thiamine.

Persons suffering with anemia may require an increased intake of iron. Persons suffering vitamin deficiencies or who have poor diets will require more vitamins A, C and riboflavin, particularly growing children in developing countries, e.g., South and Central America Such matters are familiar to physicians and nutritional experts, and usage of the compositions of the present invention may be adjusted accordingly.

The composition of the invention may also be formulated for topical use. Examples of topical composition including combination systems comprising:
NBC 0.0011 to 0.2%
L-ascorbic acid 5.0 to 20.0%

Tocopherol 0.5 to 2.0%
Rosehip Oil 0.1 to 2.0%
Rice Oil and derivatives 1 to 10%.

The above combinations have the ability to treat skin conditions such as hyperpigmentation, sunspots, solar keratosis and melasma.

The synergy of combining actives such as nanoparticulate carotenoids, L-ascorbic acid, Vitamin E, rice oil and rosehip oil when incorporated into a suitable topical formulations have the ability to saturate the nuclear receptors of melanocytes and/or binding proteins thereby reducing the production of melanin.

The performance of the above synergy may be further enhanced by also including products containing mucopolysaccharides such as at least one of these selected from the group consisting of shark cartilage, shell fish derivatives, hyaluronates, plant extracts, e.g. Licorice, Ulmus root, *Areca catechu*, soy proteins, polypeptides and glucans. The skilled person will appreciate that this list shows examples only, and is not restricted to these materials. It will be appreciated from the disclosure herein that a wide range of additional supplements and additives may be used.

The composition of the invention may be used in the relief and treatment of solar keratosis, skin protection, after sun and post laser, treatment for sunspots and hyperpigmentation. An example of a suitable formulation for such use may include:

The synergistic actives such as
NBC 0.001% to 2.0%
Tocopherol 0.1% to 5.0%
L-ascorbic acid 2.0% to 30.0%
Niacin 0.01% to 1.0%
Plant extracts
Excipients such as,
Hyaluronic acid
Formed o/w and w/o
NBC 0.001% to 5.0%
Tocopherol 0.1% to 5.0%
Alpha hydroxide acid 1% to 20%
Beta hydroxide acid 1% to 20%
Niacin 0.01% to 1.0%
Plant Extracts
Treatment of acne, eczema, psoriasis, ulcers, wound healing.
NBC 0.001% to 1.0%
Tocopherol 0.1% to 5%
Phytoserols 0.1% to 10%
Sophora Root 0.1% to 2%
Beta Glucan 0.1% to 20%
Niacin 0.01% to 1.0%
Plant based aminopeptides
Treatment pre and post laser treatments.
L-ascorbic acid
Vitamin E 0.2% to 5%
NBC 0.003% to 2%
Tretinoin 0.1% to 2%
Hyaluronic acid 0.1% to 10%
Chitin liquid 0.1% to 10%
Niacin 0.01% to 1.0%
Beta glucan
L-ascorbic acid could be replaced by using alpha hydroxyl acid 0.5% to 10%.

A combination skin treatment may include the following:
NBC 0.001 to 0.2%
L-ascorbic acid 5.0 to 20.0%
Tocopherol 0.5 to 2.0%
Rosehip Oil 0.1 to 2.0%
Rice Oil and derivatives 1.0% to 10%

The above combination has the ability to treat skin conditions such as hyperpigmentation, sunspots, lightens the skin, reduces solar keratosis.

The synergy of combining actives such as nanoparticulate carotenoids, L-ascorbic acid, Vitamin E, rosehip oil and rice oil when incorporated into a suitable topical formulations have the ability to saturate the nuclear receptors of melanocytes and/or binding proteins thereby reducing the production of melanin.

The performance of the above synergy may be further enhanced by also including products containing muccopolysaccharides such as one or more selected from the group consisting of shark cartilage, shell fish derivatives, hyaluronates, plant extracts, e.g. Licorice, Ulmus Root, *Areca Catechu*, soy proteins, polypeptides and glucans. This list shows examples only, and are not restricted to these materials.

One of the major problems facing the aging population is the increase in the incidents of nasal, oral and ophthalmic problems. Compositions of the present invention may be used to satisfy the urgent need to improve the lifestyle of these people, age 50 years plus, in the treatment of complaints such as:
(i) Oral/nasal ailments such as a dry mouth, ulcers and gingivitis; and
(ii) Ophthalmic ailments such as dry eyes, inflamed eyes and ulcers.

While a wide range of compositions of the invention may be used in such treatments interim trials indicate that a particularly preferred combination comprises a nanoparticulate carotenoid component, sodium hyaluronate, chitin and botanical extracts.

These base components or synergies could be incorporated in formulations such as:
(i) Oral treatments such as toothpaste (or similar products to clean teeth), mouth washes, mouth sprays, tablets, capsules including soft and hard capsules and caplets, pastes, sprays including aerosol sprays, gels and lozenges;
(ii) Ophthalmic treatments such as eye drops, eye sprays, ointments, creams and lotions;
(iii) Nasal treatments such as sprays, drops, lotions and creams; and
(iv) Nutritional supplements for oral administration such as tablets, capsules, syrups, powders, granules and dry drink mix compositions.

As previously explained the composition of the invention may comprise additional vitamins, minerals and other additives. These additives may be used in compositions of the invention for topical application or for oral ingestion.

Vitamin E is also a well-known antioxidant. Vitamin E can work synergistically with carotene in the composition and also with vitamin C in protecting vital cell function from normal oxidants. Vitamin E is a relatively non-toxic fat-soluble vitamin. Vitamin E is readily oxidized thereby significantly reducing its activity during periods of storage prior to ingestion. Once ingested, vitamin E is stored within the body and can contribute to the total body pool of vitamin E for up to one year.

The RDA of vitamin E in the form of dl-alpha tocopheryl acetate is 30 IU. No adverse effects of dl-alpha tocopheryl acetate have been observed at levels as high as 800 mg, with 1.0 mg of dl-alpha tocopheryl acetate being equal to 1 IU of dl-alpha tocopheryl acetate.

Mineral antioxidants that can be selected for inclusion in a nutrient composition of the invention as an optimal combination include, for example, zinc or selenium. Either or both of these minerals as well as other vitamin antioxidants well known in the art can be included in the composition of the invention.

Zinc, taken in the form of picolinate, carbonate, ascorbate, or complexed to a chelated amino acid, for example, is one mineral exhibiting antioxidant activity. Zinc also is utilized for the metabolic activity of about 200 or more enzymes and is considered important for cell division and the synthesis of DNA and polypeptides. Zinc deficiency contributes to growth retardation and even mild deficiency may limit growth in otherwise healthy children.

Zinc functions, for example, in energy metabolism as part of the lactate dehydrogenase enzyme system. Zinc also participates in immune function, as evidenced by its role in promoting enhanced would healing, and serves as an antioxidant, such as part of the superoxide dismutase enzyme system.

Zinc is important in maintaining the health of an eye's retina and is an essential part of more than 100 enzymes involved in digestion, metabolism, reproduction and wound healing. The RDA for zinc is approximately 15 mg. In one study, 80 mg of zinc was shown to be significantly better than placebo in retarding macular degeneration changes.

Selenium, taken in the form of picolinate, carbonate, ascorbate, or complexed to a chelated amino acid for example, is another mineral having antioxidant activity.

Selenium is an important component of the active sites of, for example, the enzymes glutathione peroxidase, iodothyronine 5'-deiodinase and mammalian thioredoxin reductase.

It is also present in several other mammalian selenoproteins. Both glutathione peroxidase and thioredoxin reductase catalyze reactions involved in the protection of cellular components against oxidative and free radical damage. Therefore, selenium as well as zinc and other nutrients within the compositions of the invention augment the activity of enzymes within one or more antioxidant enzyme systems of an individual. Selenium also plays a role as a mammalian cell's second line of defense against damaging cell peroxides. It performs this role as an integral part of the glutathione peroxidase enzyme system.

High potency antioxidants that can be selected for inclusion in a nutrient composition of the invention as an optimal combination include one or more of, for example vitamins minerals and antioxidants.

Alpha lipoic acid is a potent antioxidant found, for example, in the mitochondria. It acts as a coenzyme in the alpha-keto-dehydrogenase enzyme complex of the Kreb's cycle to facilitate aerobic respiration as well as participates in the metabolic pathways which regenerate de novo levels of ascorbate, alpha-tocopherol, and glutathione. Alpha lipoic acid also functions as a potent free radical scavenger. In addition to these antioxidant activities, alpha-lipoic acid also can, for example, inhibit NF-kappa B activation, HIV replication in cell cultures and reduce the severity of peripheral neuropathy in diabetes mellitus patients. Alpha-lipoic acid thus provides superior antioxidant protection due to the fact that it enhances the potency of other antioxidants in the body. Alpha-lipoic acid may be added to the nutritional or dietary supplement composition of the present invention if desired.

Acetyl L-carnitine is similarly a nutrient with potent antioxidant activity because it supports antioxidant activity under a diverse set of conditions. The acetyl moiety of the amino acid carnitine regulates fatty acid transport across the mitochondrial membrane.

The composition of the present invention also provide a nutritionally-supplemental amount of calcium. Suitable sources of calcium include calcium carbonate, calcium oxide, calcium hydroxide, calcium sulfate, calcium chloride, calcium phosphate, calcium hydrogen phosphate and calcium dihydrogen phosphate, as well as the respective organic salts of calcium, e.g., calcium citrate, calcium gluconate, calcium realate, calcium tanrate or calcium lactate and mixtures thereof. A particularly preferred calcium source are calcium citrate malate (CCM) complexes. Suitable methods for incorporating calcium into food products such as drinks are described, for example in the following documents: U.S. Pat. No. 4,737,375, issued to Nakel et al.; May, 1988; U.S. Pat. No. 4,830,862 issued to Braun et al., May 1989; and U.S. Pat. No. 4,722,847 issued to Heckert (1988); U.S. Pat. No. 5,186, 965 issued to Fox (1993); (incorporated herein by reference).

The compositions of the present invention may comprise from about 0.03% to about 0.19% calcium. Preferably the compositions comprise from about 0.05% to about 0.16%, and also preferably from about 0.1% to about 0.15% calcium.

Compositions of the invention may contain an effective amount of an iron nutritional supplement. Iron-containing preparations are used to alleviate disorders related to iron deficiency (e.g. anemia). Pregnant women, in particular, are known to require significant dietary supplementation with iron, vitamins (e.g. folic acid), and non-ferrous minerals to minimize the risk of birth deformities in the fetus, to improve the chances of a successful delivery and to improve birth weight of the fetus. Pregnant and lactating women commonly require iron to alleviate or treat iron-deficiency anemia. Indeed, various patents are directed to improving the efficacy of iron supplementation during pregnancy.

In addition to their use in pregnant and lactating women, iron supplements containing vitamins, minerals, or both are well known and are used as sources of dietary iron to treat or prevent iron deficiency in mammals. These iron supplements generally include a single form of iron, for example, an iron (II) salt (i.e. a salt containing divalent or ferrous iron), an iron (III) salt (i.e. a salt containing trivalent or ferric iron), or iron (0) powder. A preferred form of iron is carbonyl iron, Controlled release dosage forms of iron-containing nutritional supplements may be used. Controlled release may be provided in which iron (II) salt is encapsulated in or mixed with a release rate modifying matrix, one of certain iron (III) salts which exhibit poor solubility, carbonyl iron or one of the other metallic forms of iron (which also exhibit poor solubility), a certain crystalline form of iron oxide, or an iron salt or carbonyl iron complexed with a protein, an amino acid, an organic acid, a natural polymer, an anionic complexing agent, or a synthetic polymer.

Examples of iron compounds which can be used in the nutritional supplement include, without limitation, ferrous fumarate, ferrous sulfate, ferrous folate, an iron dextran, ferric oxyhydroxide dextran, a chitosan derivative of iron, an oligosaccharide derivative of iron, ferrous acetyl salicylate, ferrous gluconate, ferrous diphosphate, carbonyl iron, ferric orthophosphate, ferrous glycine sulfate, ferrous chloride, ferrous ammonium citrate, ferric ammonium citrate, ferric ammonium tartrate, ferric phosphate, ferric potassium tartrate, ferric albuminate, ferric cacodylate, ferric hydroxide, ferric pyrophosphate, ferric quinine citrate, ferric valerate, saccharated iron oxide, iron oxide, ferric chloride, ferrous iodide, ferrous nitrate, ferrous glycerophosphate, ferrous formate, an amino acid and iron salt, an iron salt of a protein hydrolysate, ferrous lactate, ferrous tartrate, ferrous succinate, ferrous glutamate, ferrous citrate, ferrous pyrophosphate, ferrous cholinisocitrate, ferrous carbonate, an iron-sugar-carboxylate complex, ferrous sucrate-malate, ferrous sucrate citrate, ferrous fructate-citrate, ferrous sucrate-ascorbate, and ferrous fructate-ascorbate.

The recommended daily allowance of elemental iron for women, as established by the United States Food and Drug Administration Center for Food Safety and Applied Nutrition (revised 1989), is about 15 milligrams per day. Ingestion of 30 milligrams of iron per day is recommended for pregnant women. In addition, pregnant women are recommended to ingest at least about 1 milligram of folic acid during pregnancy, and preferably during weeks or months preceding pregnancy. The compositions and methods described herein are useful for providing iron to mammals, and are intended to be used, for example, to administer iron to women, including pregnant women, women anticipating pregnancy, and lactating women. The composition of the invention may contain up to about 100 milligrams of iron preferably from 1 to 100 milligrams and more preferably at least about 10 milligrams.

Copper, like zinc, is another important cofactor for metalloenzymes, and is a second necessary cofactor for superoxide dismutase.

Copper in the form of cupric oxide is preferred in compositions of the invention to help prevent zinc induced copper deficiency anemia, although other forms of copper such as for example copper gluconate may alternatively be used or used in combination with cupric oxide in the subject composition.

Phenolic compounds (including polyphenolics) such as for example but not limited to oligomeric proanthocyanidins are additional useful antioxidants. Oligomeric proanthocyanidins are found naturally in grape seeds. Phenolic compounds may be added to the nutritional or dietary supplement composition of the present invention if desired.

Phytonutrients including phytoestrogen, phytoesterols and the like may be used in the invention.

Soybeans are the richest food source of a type of "phytoestrogen" called isoflavones (genistein, daidzein and glycitin). These isoflavones bind to estrogen receptors sites acting like a mild form of estrogen, thus bringing a number of benefits to the body.

Anthocyanosides are useful antioxidants found naturally in bilberry fruit. Anthocyanosides may be added to the nutritional or dietary supplement composition of the present invention if desired.

The above are listed as examples only, and not restricted to these application forms.

Compositions of the invention may comprise an effective amount of Vitamin C. Vitamin C is a well-known water-soluble antioxidant and provides advantages for compositions of the invention used in skin treatment food supplements and in treatment of eye ailments. Humans depend on external sources of vitamin C to meet their vitamin C requirements. Vitamin C in the form of ascorbate is found in the aqueous humor of human eyes.

There are many papers that confirm carotenoids sourced from sea alga Dunaliell Salina offer the most bio effective balance of carotenoids for oral and topical applications. These papers are also supported by clinical studies statistically proving that carotenoids play a very important function or protecting humans and animals from the adverse effect of the sun by protecting the immune system.

Human trials show that beta-carotene:
Prevented UV light-suppressed immune function (DTH) in young and elderly men (Fuller, C J et al. *AM J Clin Nutr.* 1992; 56:684 and Herraiz et al. *J Am Coll Nutr.* 1998; 17:617)
Prevented age related decline in natural killer cell (NK) activity in elderly men (Santos, M S et al. *Am J Clin Nutr.* 1996:54:772)
Increases lycopene in stimulated expression of cell surface molecules that initiate immune response (Hughes, D A. *Proc Nutr Soc.* 1999; 58:713)
In a mixed carotenoid supplement (7 mg/d) restored immune function suppressed by low carotenoid diets in women (Kramer, T R and Burrin, D J. *Am J Clin Nutr.* 1997; 65:871-875).

The use of nanoparticulate carotenoids in these applications significantly increases the efficacy of the carotenoid composition and may provide several of the major carotenoids found in healthy diets of fruit and vegetables. The alpha and beta-carotene found in nanoparticulate carotenoid compositions provide a safe and natural source of Vitamin A. Beta-carotene and other carotenoids found in nanoparticulate carotenoid compositions act as antioxidants to stop free radicals than can damage cells.

Nanoparticulate carotenoids increase Gap Junctional Communication (GJC).

The protein channels between connected cells allow the exchange of small water-soluble molecules and ions. This exchange is important for cell communication and signalling, nutrient exchange, control of cell growth, cell differentiation, secretion of hormones and growth. Beta-carotene was found to be most potent in increasing GJC, independent of Vitamin A activity or antioxidant actions.

By up regulating GJC, carotenoids help maintain normal metabolic processes to keep humans healthy (Stahl, W and Sles, H. Inernat J, *Vit Nutr Res.* 1998; 68:354-359).

A specific example of a food supplement may include

| Nanoparticulate beta carotene | 0.001 to 0.1% |
| L-ascorbic acid | 0.5 to 2.0% |
| Vitamin E together with a suitable carrier. | 0.01 to 2.0% |

Where the combination of these actives improves the oral and topical performance to the total dose level can be reduced resulting in a safer product. This dose form could be in soft or hard gel to maintain the stability of the vitamin C and L-ascorbic acid.

L-ascorbic acid is not stable when exposed to moisture. or formulas in tablets or water phase systems, where L-ascorbic acid is converted to d-ascorbic acid, the less bio effective form of L-ascorbic acid.

We also know that both magnesium ascorbyl phosphate and ascorbyl palmitate do not offer the same bio effectiveness as L-ascorbic acid, even though these materials are stable in water-based systems.

Some of these papers also suggest that by combining these carotenoids orally and topically this inside out side approach offers a more effective approach to reducing damage to the skin.

The composition of the invention may provide the carotenoid in the form of an oil-in-water emulsion or dispersions.

The oil-in-water emulsion provides a water-dispersible carotenoid composition. I Beta-carotene and other carotenoids are more oil soluble than water-soluble and preferably exist as a dispersion of the nanoparticles. The oil phase provides a protective coating, barrier, or droplet around the carotenoid providing stability and minimising decomposition. Preferably further, the water insoluble carotenoid component constitutes from 0.1% to 10% by weight of the agent. It is particularly preferred that the water insoluble carotenoid component constitutes from 1% to 5% by weight of the agent.

The carrier medium for the carotenoid in the emulsion will typically also include an emulsifier. Preferably, the emulsifier is a non-ionic emulsifier such as a polyalkylene oxide condensate such as a polysorbate and glycerol fatty acid esters and acetylated esters of fatty acids. Glycerol mono-oleate is a particularly preferred emulsifier.

Carotenoids are an important factor in the production of meat, poultry, fish, and crustacean with regard to nutrition.

Carotenoids importance has increased with the trend to increased intensive farming. Intensive farming increases the possibility of diseases in the animals through stress, poor reproduction resulting in quality of meat and reduction in productivity. The carotenoid composition of the invention may be used to improve the quality of animal produce and/or improve animal health.

Intensive farming has been used in areas of pork, poultry, fish and aquaculture have been using antibiotics and other actives to reduce the downside effects of this farming practice.

Many of the additives currently used in animal feed have the potential for causing adverse effects when consumed by humans and there is a need to use alternative materials which are safer and more acceptable to the industry, regulatory and health authorities. For example the use of human antibiotics in animal feed has significant deleterious effects on the activity of these drugs in human medicine.

Some vitamins can be synthesized in the body and therefore do not need to be added to the animal's diet. Fat soluble vitamins can be stored in the animal's body, reducing the need for daily supply, however water soluble vitamins cannot be stored and therefore need to be supplied on a daily basis.

Vitamin content of feeds varies with the quality of feed. A feed may contain an essential vitamin but it may have a low bio-availability in metabolism. It is generally recommended that vitamin premixed be used at the appropriate levels in livestock feeding to ensure a ready supply of essential vitamins are available.

The animal feed in accordance with the invention will preferably contain from 1 ppm to 1% by weight of nanoparticulate carotenoid component and more preferably from 1 ppm to 0.3% by weight of the carotenoid component. The carotenoid is typically incorporated as a concentrate in the oil in which it is prepared.

Specific vitamins have specific functions and are involved in a number of metabolic processes, deficiency symptoms are an indication that basic metabolic processes in the body have been disturbed.

Carotene is converted into vitamin A, as such carotene is considered a precursor of vitamin A, with different animal species convert carotene to vitamin A at different rates. True vitamin A is not found in animal feeds, however, stable stock feed containing vitamin A can provide a suitable balance.

In animals vitamin A is stored in the liver and fatty tissue of the body. Animals can use this stored vitamin A during periods of feeding when the diet is deficient in carotene. For example, a horse can go for up to 3-6 months and sheep up to 200 days when vitamin A is deficient in their diet.

Night blindness is a symptom of severe vitamin A deficiency. Animals may become permanently blind because of a vitamin A deficiency, or may suffer eye infections and constriction in the optic nerves in less severe cases.

Excessive watering of the eyes and cornea ulcerations are indications of possible vitamin A deficiency. Keratinisation of the epithelial tissue, which causes lowered resistance to infections, is common with vitamin A deficiency.

Diarrhoea, reduced appetite, poor growth and weight loss are also indicators of vitamin A deficiency, along with reproductive problems, poor concept on, reduced fertility in males, shortened gestation, retained placenta and still born as additional indicators.

Nanoparticulate carotenoid compositions of the present invention provide an improved source of pro-vitamin A. Nanoparticulate carotenoids provide improved bio-availability, improved sustained release over time, reduce dose levels and reduce dose costs.

Nanoparticulate carotenoid compositions of the invention have the ability to replace many actives currently being used to maintain health.

The invention will now be described with reference to the following examples. It is to be understood that the examples are provided by way of illustration of the invention and that they are in no way limiting to the scope of the invention.

EXAMPLES

The examples describe compositions with respect to the attached drawings. In the drawings.

METHOD

A suspension is prepared by mixing between 20-40% by weight of carotene in a suitable oil in a mill feed tank equipped with a high speed mixer and dispersion blade, the tank is purged with nitrogen to exclude oxygen prior to milling and a blanket is kept on the tank during processing.

Preferred oil soluble anti oxidants can be added and dissolved before mixing in carotene powder. Milling is carried out at low temperatures using a cooled bead mill such as a Drais Superflow 85 or a Hockmeyer HM20 with 0.3 mm PSZ beads in a recirculating mode until a particle size of less than 100 nm, preferably less than 50 nm is achieved.

Milling by this procedure produces stable suspensions, which have shelf stability in excess of 2 years with no sign of re crystallisation, settling or loss of activity. Product is stored in sealed containers, which completely block out light.

Raw Material Source: Betatene (Cognis)

We have used a 30% suspension of beta-carotene produced from *dunaliella salina* algae suspended in capric caprylic triglyceride with an initial crystal size of 20 micron average size.

The nanobeta-carotene prepared in this example is used in subsequent examples where it is referred to as NBC.

Example 1

Figure 1:
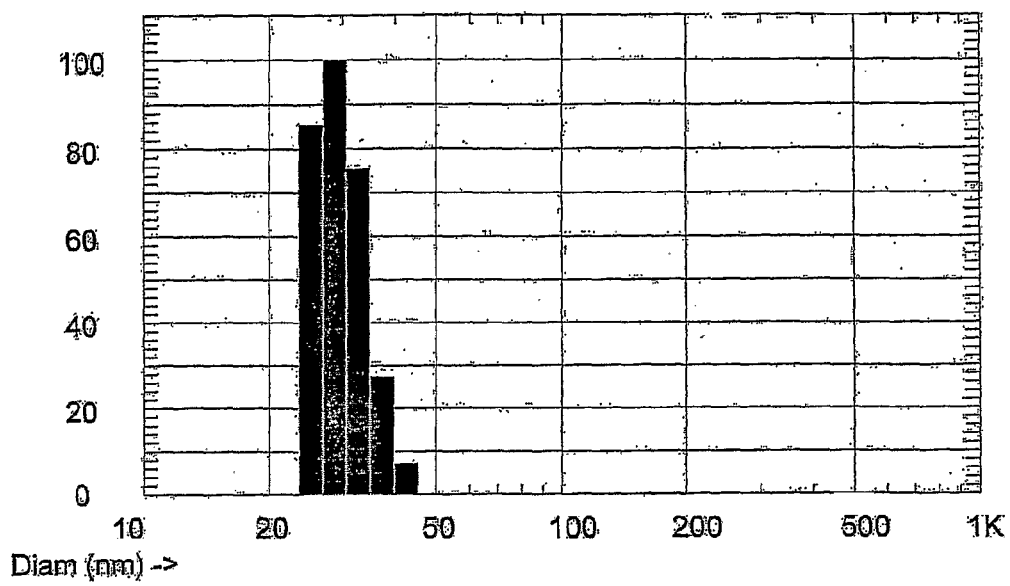
FIG. 1 is a bar chart showing the particle size of the composition of Example 1.

A carotene suspension containing 30% beta carotene in capric caprylic triglyceride was milled for 6 hours in a Laboratory Hockmeyer HM ¼ cage mill using a bead charge of 140 gms PSZ beads of size 0.7 mm. Milling was carried out at high speed. Particle size was determined using a laser particle analyser and the particle size was 29.8 nm. Detailed analysis results are shown below and a graph of the results is shown in FIG. 1.

Nicomp Summary:

Peak #1: Mean Diameter=29.5 nm, Standard Deviation=4.9 nm (16.6%) Number=100.0%

Peak #2: Mean Diameter=437.6 nm, Standard Deviation=– 1.$ nm (–1.$ %) Number=0.0%

Mean Diameter=29.8 nm Fit Error=41.553 Residual=0.000

Nicomp Scale Parameters:
Min. Diameter=10 nm Plot Size=36
Smoothing=3 Plot Range=100
Gaussian Summary:
Mean Diameter=57.6 nm Chi Squared=7.922
Standard Deviation=37.3 nm (64.8)% Baseline Adj.=0.000%
Coeff. of Var'n=0.648 Mean Diff. Coeff.=2.48E-009 cm2/s
Run Time=0 Hr 32 Min 37 Sec Wavelength=632.8 nm
Count Rate=1 KHz Temperature=20° C.
Channel #1=2.2 K Viscosity=30.000 cp
Channel Width=600.0 uSec Index of Ref.=1.447

The nanobeta carotene prepared in this example is used in subsequent examples where it is referred to as NBC.

Example 2

Figure 2:
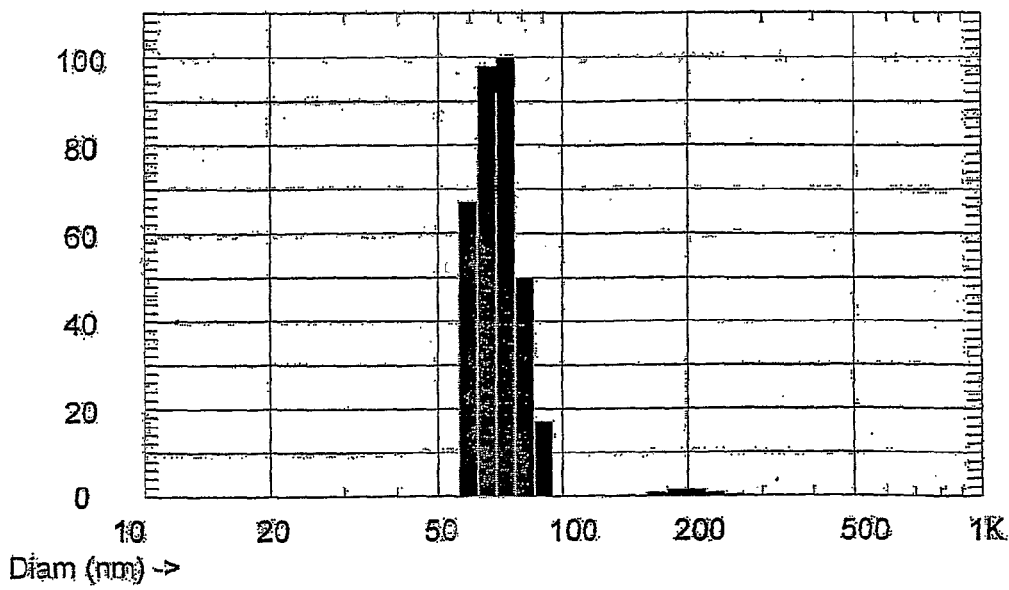
FIG. 2 is a bar chart showing the particle size of the composition of Example 2.

The raw material used for milling was micro algae *Haematococcus Pluvialis* Naturose from Cyanotech as a 30% suspension of astaxanthin in soya lecithin. The composition was milled at high speed for 6 hours using a Laboratory HM ¼ cage mill with a bead charge of 140 gms of PSZ beads of 0.7 mm size. Particle size 20-80 nm was examined using a laser particle analyser and the particle size was 72.3 nm. Detailed analysis results are shown below and a graph of the results is shown in FIG. 2.
Nicomp Summary:
Peak #1: Mean Diameter=70.2 nm, Standard Deviation=7.5 nm (10.7%) Number=98.4%
Peak #2: Mean Diameter=199.3 nm, Standard Deviation=24.8 nm (12.5%) Number=1.6%
Mean Diameter=72.3 nm Fit Error=1.832 Residual=34.149
Nicomp Scale Parameters:
Min. Diameter=10 nm Plot Size=45
Smoothing=3 Plot Range=100
Gaussian Summary:
Mean Diameter=72.2 nm Chi Squared=46.646
Standard Deviation=50.5 nm (65.5)% Baseline Adj.=0.050%
Coeff. of Var'n=0.655 Mean Diff. Coeff.=5.55E-008 cm2/s
Run Time=0 Hr 38 Min 20 Sec Wavelength=632.8 nm
Count Rate=121 KHz Temperature=20° C.
Channel #1=197.9 K Viscosity=1.002 cp
Channel Width=20.0 uSec Index of Ref.=1.330

Example 3

Figure 3:
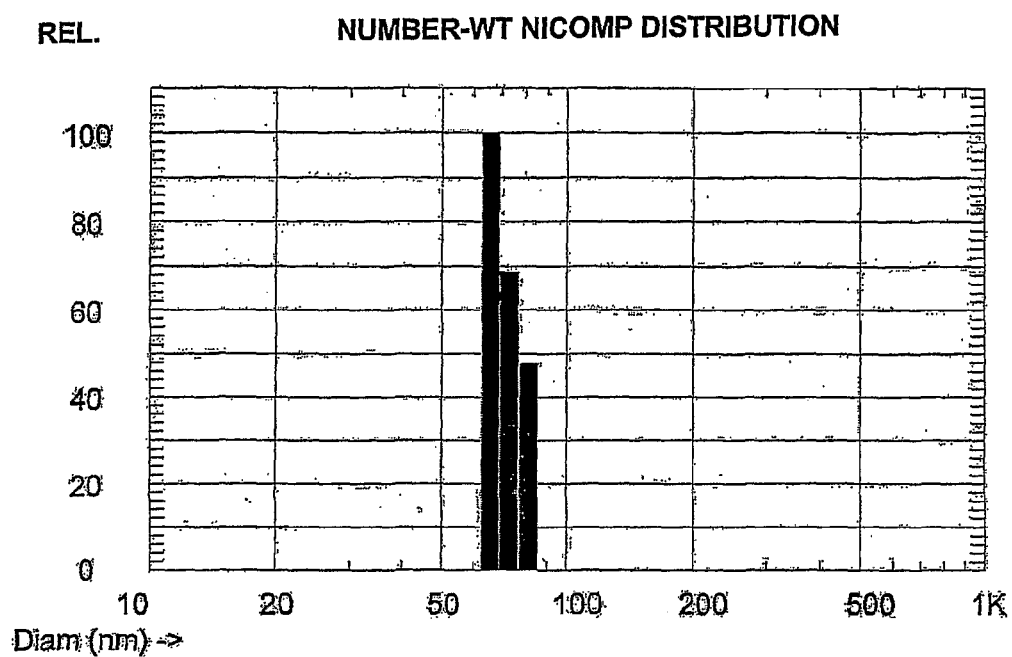
FIG. 3 is a bar chart showing the particle size of the composition of Example 3.

A 30% suspension beta-carotene in grape seed oil was milled at high speed for 6 hours using the equipment described in Example 1. Particle size 20-80 nm was examined with laser particle analyser and the particle size was 71.5 nm. Detailed analysis results are shown below and a graph of the results is shown in FIG. 3.
Nicomp Summary:
Peak#1: Mean Diameter=71.5 nm, Standard Deviation=5.1 nm (7.1%) Number=100.0%
Mean Diameter=71.5 nm Fit Error=41.263 Residual=0.000
Nicomp Scale Parameters:
Min. Diameter=10 nm Plot Size=45
Smoothing=3 Plot Range=100
Gaussian Summary:
Mean Diameter=26.9 nm Chi Squared=7.476
Standard Deviation=34.2 nm (127.0)% Baseline Adj.=0.000%
Coeff. of Var'n=1.270 Mean Diff. Coeff.=6.65E-009 cm2/s
Run Time=0 Hr 15 Min 15 Sec Wavelength=632.8 nm
Count Rate=11 KHz Temperature=20° C.
Channel #1=1.2 K Viscosity=24.000 cp
Channel Width=13.0 uSec Index of Ref.=1.447

Example 4

Figure 4:
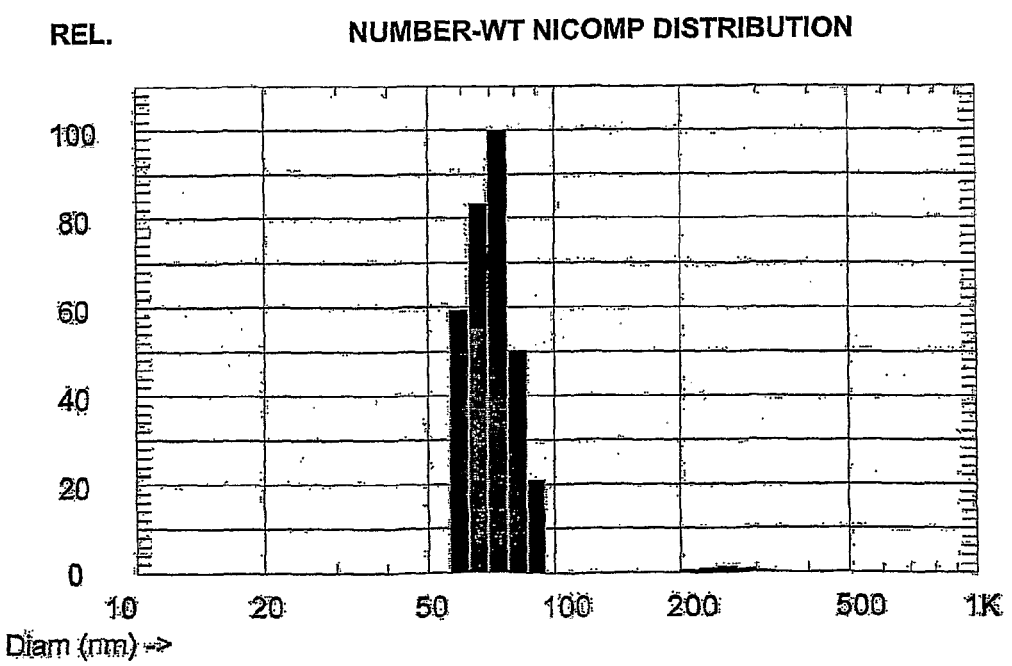
FIG. 4 is a bar chart showing the particle size of the composition of Example 4.

A 30% suspension of beta carotene in grape seed oil (500 gms) with added anti oxidant tocopherol (60 gms) was milled at high speed for six hours using the equipment described in Example 1. Particle size 20-80 nm was examined with laser particle analyser and the particle size was 73.6 nm. Detailed analysis results are shown below and a graph of the results is shown in FIG. 4.
Nicomp Summary:
Peak #1: Mean Diameter=70.9 nm, Standard Deviation=7.6 nm (10.8%) Number=98.6%
Peak #2: Mean Diameter=255.8 nm, Standard Deviation=29.6 (11.6%) Number=1.4%
Mean Diameter=73.6 nm Fit Error=3.136 Residual=16.171
Nicomp Scale Parameters:
Min. Diameter=10 nm Plot Size=45
Smoothing=3 Plot Range=100
Gaussian Summary:
Mean Diameter=50.6 nm Chi Squared=4.313
Standard Deviation=27.6 nm (54.5)% Baseline Adj.=0.000%
Coeff. of Var'n=0.545 Mean Diff. Coeff.=8.46E-008 cm2/s
Run Time=0 Hr 20 Min 24 Sec Wavelength=632.8 nm
Count Rate=39 KHz Temperature=20° C.
Channel #1=29.7 K Viscosity=1.002 cp
Channel Width=20.0 uSec Index of Ref.=1.330

Typical examples of skin care products and other products using the nano milled beta carotene are as follows:

Example 5

Formulation moisturizer—o/w or w/o

| Phase A | |
|---|---|
| Guar gum | 1.4% |
| Glycerine | 6.7% |
| Water | Too 100.0% |

Pre-mix guar gum and glycerine. Add Water and stir until uniform.

| Phase B | |
|---|---|
| ELS B4 emulsifier | 4.0% |
| Emerest emulsifier | 1.5% |
| Beantree | 5.0% |
| Myritol 318 | 5.0% |
| MacPaste (Macadamia Paste) | 2.0% |
| Phase A | 81.999% |

Heat to 45° C., while stirring add A to Phase B. Mix until smooth.

| Phase C | |
|---|---|
| Nano Beta Carotene NBC | 0.001% |
| ELS B4 emulsifier | 0.5% |
| Preservative | q.s |
| Total | 100.0% |

Pre-mix, while stirring add to Phase AB, mix until uniform and smooth.

This formulation has the flexibility and stability to be used for the basic treatment of a wide range of conditions, by using different combinations of actives and excipients in Phase C. For example;

For the treatment of:
Wounds
Ulcers
Solar keratosis
Sun burn
The following alterations to Phase C can be made.

| Phase C | |
|---|---|
| Nano Beta Carotene | 0.1% |
| Tocopherol | 1.0% |
| Dioctyl Malate | 1.0% |
| Hyaluronic Acid | 1.0% |

For the treatment of:
Eczema
Acne
The following alterations to Phase C can be made.

| Phase C | |
|---|---|
| Nano Beta Carotene | 0.1% |
| Tocopherol | 1.0% |
| Dioctyl Malate | 1.0% |
| Hyaluronic Acid | 1.0% |
| *Sophora* Root | 1.0% |

For the treatment of sun spots the following alterations to Phase C can be made.

| Phase C | |
|---|---|
| Nano Beta Carotene | 0.1% |
| Tocopherol | 1.0% |
| Dioctyl Malate | 1.0% |
| Chitin Liquid | 1.0% |
| Licorice/*Morus Alba*/*Scutelaria* Extract | 1.0% |

Example 6

Sunscreen

Oil in Water or Water in Oil Formulation

| Phase A | |
|---|---|
| Cosmedia SP anionic gel | 1.5% |
| Glycerine | 5.0% |
| Water | 93.3% |
| CA24 | 0.2% |
| Sub Total | 100.0% |

Pre mix glycerine with Cosmedia SP, while stirring add water continue stirring to form a smooth gel, then add CA24.

| Phase A | 62.0% |
|---|---|

| Phase B | |
|---|---|
| ELSB4 emulsifier | 1.0% |
| Emerest emulsifier | 5.0% |
| Elefac 1-205 | 5.0% |
| MacPaste | 5.0% |
| Stable Sunsorb ZnO E65/30/22 | 15.0% |
| Sunsorb TiO2 E70/200 | 3.0% |
| *Polygonum* Extract | 2.0% |
| Beantree oil | 2.0% |
| Total | 100.0% |

Heat Phase B to 45 C. While stirring add to Phase A.
Continue stirring until oxides have been blended into the product and form a uniform emulsion.

| Phase C | |
|---|---|
| Add nano size beta-carotene dispersed in capric caprylic triglyceride or other edible oils | 0.001% |

Note: To formulate a water in oil cream or lotion, reverse the emulsifiers and ratios, e.g. ELSB4 at 5.0% in water phase and Emerest at 1.0% in oil phase.

Example 7

Natural Sunscreen Modified

Oil in Water or Water in Oil Formulation

| Phase A | |
|---|---|
| Guar gum cationic gel | 1.0% |
| Glycerine | 6.0% |
| CA 24 preservative | 0.2% |
| Water | 92.8% |
| Sub Total | 100.0% |

Pre mix glycerine with water, while stirring add guar gum and continue stirring until dispersed.

| Phase B | |
|---|---|
| Phase A | 62.5% |
| ELS B4 emulsifier | 5.0% |

While stirring add Phase B to Phase A to form a uniform emulsified gel.

| Phase C | |
|---|---|
| Emerest emulsifier | 1.5% |
| Bean tree oil | 5.0% |
| Myritol 318 | 5.0% |
| MacPaste (Macadamia paste wax) | 2.0% |

Add to phase AB while stirring.

| Phase D | |
|---|---|
| Stable Sunsorb ZnO E65/30/22 | 12.0% |
| Sunsorb TiO2 E70/200 | 7.0% |
| Total | 100.0% |

While stirring add to Phase ABC. Stir until smooth.
Continue stirring until oxides have been blended into the product.
If you wish you have the option of adding each incipient in Phase C individually to Phase A.

| Phase E | |
|---|---|
| Nano size beta-carotene dispersed in capric caprylic triglyceride (NBC) or other edible oils | 0.001% |

You also have the option to formulate as either w/o or o/w by reversing the percentage of emulsifiers.

Example 8

Natural Base Cream

Oil in Water—Water in Oil Formulation

| Phase A | |
|---|---|
| Guar gum C261N | 2.0% |
| Citric Acid | 0.1% |
| Water | 99.7% |
| Sub Total | 100.0% |

Pre mix, add citric acid until clear.

| Phase B | |
|---|---|
| Phase A | 84.5999% |
| ELS B4 emulsifier | 5.0% |

While stirring add Phase B to Phase A to form a stable cream.

| Phase C | |
|---|---|
| Bean tree oil | 3.0% |
| Myritol 318 | 5.0% |
| Conarom H3 | 0.4% |
| Vitamin E | 1.0% |
| Nano size beta-carotene dispersed in capric caprylic triglyceride (NBC) or other edible oils | 0.0001% |
| ELSB4 emulsifier | 1.0% |
| Total | 100.0% |

Pre-mix then add to phase AB while stirring. Stir until smooth.
Note: It is recommended that you heat all phases to 30° C., this will improve the formulation.

Example 9

Anhydrous Formulation

Anhydrous formulations are sometimes preferable options when treating various skin conditions, particularly when containing actives that are not stable when water is present.
For the treatment of:
Hyperpigmentation
Sun spots
Eczema
Acne
Pre and post laser treatment

| Phase A | |
|---|---|
| MacPaste | 5.0% |
| Grape seed Paste | 10.0% |
| MCT | 10.0% |
| Olive Oil | 10.0% |
| Bean tree | 51.5% |

Heat to 50° C., stir until uniform.

| Phase B | |
|---|---|
| NBC | 0.1% |
| 50% L-Ascorbic Acid | 10.0% |
| Tocopherol | 1.0% |
| Arbutin | 0.8% |
| *Sophora* Root | 0.6% |
| Dioctyl Maleate | 1.0 |

Pre-mix and add to Phase A, continue stirring until dispersed.

Example 10

Gel System

This system has been designed for use in oral applications for the treatment of such conditions such as:
Dry mouth
Mouth ulcers
Inflammations

| Phase A | |
|---|---|
| Guar gum | 1.0% |
| Glycerine | 3.0% |
| Hyaluronic Acid | 2.0% |
| Fructan | 1.0% |
| Water | Too 100 |

Pre-mix guar gum with glycerine and add to water. Stir until dispersed, while stirring add other products. Continue stirring until dispersed.

| Phase B | |
|---|---|
| NBC | 0.1% |
| Tocopherol | 0.5% |
| Plant extracts such as | |
| *Gingko Biloba* | 1.0% |
| Soy Bean | 1.0% |

-continued

| Phase B | |
|---|---|
| Wild Mint | 1.0% |
| Flavour | q.s |
| Preservative | q.s |

Pre-mix, add to Phase A while stirring. Stir until dispersed.

The viscosity of the gel can be varied, so this gel base may also be used in ophthalmic applications for the treatment of such conditions as dry eye and nasally for dry nose, by adjusting the viscosity so the formula could be used in a spray or drop type dose system.

Example 11

The following composition max be prepared form use as a skin treatment following exposure to damaging radiation from the sun, laser treatment or radiotherapy:
NBC 0.001% to 2.0%
Tocopherol 0.1% to 5.0%
L-ascorbic acid 2.0% to 30.0%
Niacin 0.01% to 1.0%
Plant extracts
Excipients such as,
Hyaluronic acid

Example 12

The following composition may be prepared for use in treatment of acne, eczema, psoriasis, ulcers, wound healing:
NBC 0.001% to 1.0%
Tocopherol 0.1% to 5%
Phytoserols 0.1% to 10%
Sophora Root 0.1% to 2%
Beta Glucan 0.1% to 20%
Niacin 0.01% to 1.0%
Plant based aminopeptides

Example 13

The following skin treatment may be prepared in the form of an o/w of w/o emulsion using suitable aqueous and organic carrier phases and the respective oil-in-water or water-in-oil emulsifier system:
NBC 0.001% to 5.0%
Tocopherol 0.1% to 5.0%
Alpha hydroxide acid 1% to 20%
Beta hydroxide acid 1% to 20%
Niacin 0.01% to 1.0%
Plant Extracts

Example 14

A food supplement for incorporation into a drink or a powder or paste for consumption with food may be prepared having the following components in the amounts by weight listed:

| NBC | 0.001 to 0.1% |
|---|---|
| L-ascorbic acid | 0.5 to 2.0% |
| Vitamin E | 0.01 to 2.0% |

Clinical Trials

We have a number clinical trials being carried out in Australia for the treatment and relief of a wide range of indications. These trials are showing promise for the relief and treatment of the following:
Solar keratosis
Pre and post laser treatments
Erythema
Skin protection
Sunspots and hyper pigmentation
Photo damage
Dry skin
Eczema
Wound healing These trials involve 20 to 100 people, aged between from 30 and above, both males and females.

We have photographic results from some of these trials that indicate and support the claims being made when using a combination of NBC, Vitamin E and L-ascorbic acid.

We believe it is the combination of various actives and excipients that provides the synergistic effect to improve overall performance. Combined with the selected base formulations:
Oil in water
Water in oil
Anhydrous
Vitamins E and C, and Beta-Carotene as Antioxidants Tocopherols (vitamin E), l-ascorbic acid and beta-carotene react with free radicals, in particular peroxyl radicals, and with the singlet oxygen molecule, which is the basis for their function as antioxidants. RRR-alpha-Tocopherol is the major peroxyl radical scavenger in biological lipids, such as membranes or low-density lipoproteins. Ascorbic acid is present in aqueous phases such as cytosol and plasma and can reduce the tocopherol radical, it also has several metabolically important cofactor functions in enzyme reactions. Beta-carotene exerts antioxidant functions in lipid phases by quenching singlet oxygen molecules or free radicals. There are differences in tissue carotenoid patterns, extending also to the distribution between the all-trans and cis isomers of the various carotenoids.

Our clinical trials are indicating that there are synergies when incorporating nanoparticulate carotenoids in formulations comprising Vitamin E, Vitamin B, Vitamin C (L-ascorbic acid) and a nano emulsifier.

These combinations tend to support each other to increase bio effectiveness in topical and oral applications such as Oral medicines, Opthalmics, Wound healing, Laser treatment, Skin protection, Eczema, Ulcers, Sunspots, Solar keratosis and Burns.

These synergistic properties are not restricted to the above actives for topical applications as we have found that the combination of nanoparticulate carotenoids, Vitamin E and Vitamin C have the ability to improve dermal bio availability as the performance of other materials such as one or more of the group of Vitamin B, Tretinoin, Phytoesters, Peptides, Amino acids, Mucopolysaccharides, Shark cartilage, Shell fish derivatives, Hyaluronates, Plant extracts, e.g. Licorice, Ulmus Root, *Areca catechu*, Soy proteins, Polypeptides and Rice oil.

The above list shows examples only, and are not restricted to these materials or their derivatives.

Trials for treating or relieving the effects of psoriasis in topical products combining NBC, hyaluronic acid, chitin liquid and hydroxy acids with various plant extracts When applied topically to the hand and other joint areas have reduced the effect of osteo arthritis, simultaneously giving relief to psoriasis.

The invention claimed is:

1. A process for preparing a carotenoid composition comprising:
   providing at least one solid beta-carotene sourced from *Dunaliella salina* algae;
   forming a composition consisting of the solid beta-carotene and an oil; and
   milling the composition to reduce the particle size of the beta-carotene to a size smaller than 100 nanometers, wherein said milling is conducted in the oil free of water and wherein the oil comprises at least one selected from the group consisting of fatty acid esters of $C_6$ to $C_{22}$ fatty acids.

2. A process according to claim 1 wherein the fatty acid esters of C6 to C22 fatty acid ester acids is selected from mono-, di-, tri-glycerides and mixtures thereof.

3. A process according to claim 1 wherein the beta-carotene is present in the composition in the range of from 1 to 80% by weight of beta-carotene based on the total weight of the composition.

4. A process according to claim 1 wherein the milling occurs at a temperature of less than 50° C.

5. A process according to claim 1 further comprising combining the resulting carotenoid composition with one or more dermally acceptable excipients to provide a skin care composition.

6. A process according to claim 1 further comprising combining the milled beta-carotene in oil with one or more pharmaceutically acceptable excipients to provide a composition for oral, nasal, ocular or parenteral administration in the form of a tablet, capsule, lozenge, spray, liquid or paste.

7. A process according to claim 1 wherein the oil comprises at least one of capric and caprylic glycerides produced from vegetable sources.

8. A process according to claim 1 wherein the beta-carotene particles are milled to provide a size in the range of from 2 to 50 nanometers.

9. A process for preparing a carotenoid composition comprising:
   forming a composition consisting of solid beta-carotene and an oil; and
   milling the composition to reduce the particle size of the beta-carotene to a size smaller than 100 nanometers, wherein said milling is conducted in the oil free of water and wherein the oil comprises at least one selected from the group consisting of fatty acid esters of $C_6$ to $C_{22}$ fatty acids.

10. A process according to claim 9 wherein the fatty acid esters of C6 to C22 fatty acids is selected from mono-, di-, tri-glycerides and mixtures thereof.

11. A process according to claim 9 wherein the oil comprises at least one of capric and caprylic glycerides produced from vegetable sources.

12. A process according to claim 9 wherein the beta-carotene particles are milled to provide a size in the range of from 2 to 50 nanometers.

13. A process according to claim 9 wherein the beta-carotene is present in the composition in the range of from 1 to 80% by weight of beta-carotene based on the total weight of the composition.

14. A process according to claim 9 wherein the milling occurs at a temperature of less than 50° C.

15. A process according to claim 9 further comprising combining the resulting carotenoid composition with one or more dermally acceptable excipients to provide a skin care composition.

16. A process according to claim 9 further comprising combining the milled beta-carotene in oil with one or more pharmaceutically acceptable excipients to provide a composition for oral, nasal, ocular or parenteral administration in the form of a tablet, capsule, lozenge, spray, liquid or paste.

* * * * *